(12) United States Patent
Li et al.

(10) Patent No.: US 11,758,818 B2
(45) Date of Patent: Sep. 12, 2023

(54) TRANSPARENT PIEZOELECTRIC SINGLE CRYSTAL PREPARATION METHOD

(71) Applicants: Xi'an Jiaotong University, Shaanxi (CN); Penn State Research Foundation, University Park, PA (US)

(72) Inventors: Fei Li, Shaanxi (CN); Chaorui Qiu, Shaanxi (CN); Zhuo Xu, Shaanxi (CN); Bo Wang, University Park, PA (US); Long-Qing Chen, University Park, PA (US); Shujun Zhang, University Park, PA (US); Thomas R. Shrout, University Park, PA (US)

(73) Assignees: XI'AN JIAOTONG UNIVERSITY, Shaanxi (CN); THE PENNSYLVANIA STATE UNIVERSITY, University Park, PA (US)

( * ) Notice: Subject to any disclaimer, the term of this patent is extended or adjusted under 35 U.S.C. 154(b) by 888 days.

(21) Appl. No.: 16/541,309

(22) Filed: Aug. 15, 2019

(65) Prior Publication Data

US 2021/0050507 A1 Feb. 18, 2021

(51) Int. Cl.
*H10N 30/853* (2023.01)
*A61B 5/00* (2006.01)
(Continued)

(52) U.S. Cl.
CPC ....... *H10N 30/8548* (2023.02); *A61B 5/0095* (2013.01); *H10N 30/045* (2023.02); *H10N 30/06* (2023.02); *H10N 30/877* (2023.02)

(58) Field of Classification Search
CPC ... H01L 41/1875; H01L 41/257; H01L 41/29; H01L 41/18; H01L 41/37
See application file for complete search history.

(56) References Cited

U.S. PATENT DOCUMENTS

| 3,773,898 A | * | 11/1973 | Aizu | ...................... H04R 17/00 310/345 |
| 5,702,629 A | * | 12/1997 | Cui | ......................... H01L 41/37 310/317 |

(Continued)

FOREIGN PATENT DOCUMENTS

| CN | 112786776 A | * | 5/2021 | |
| CN | 113801412 A | * | 12/2021 | |
| WO | WO-2005035840 A1 | * | 4/2005 | ............. C30B 11/00 |

Primary Examiner — Jeffrey T Carley
(74) Attorney, Agent, or Firm — Tutunjian & Bitetto, P.C.

(57) ABSTRACT

A method of preparing a piezoelectric single crystal with high piezoelectricity and near- perfect transparency. The method includes depositing electrodes on two opposition surfaces of a piezoelectric single crystal which is a ferroelectric crystal; AC-poling the piezoelectric single crystal through the electrodes by repeatedly changing polarity of an AC electric field; and after polarization, removing the electrodes on the two opposition surfaces of the piezoelectric single crystal and then depositing Ag nanowire or indium tin oxide (ITO) as electrodes on the two opposition surfaces of the piezoelectric single crystal. Repeatedly changing the polarity of the polarized electric field can increase the domain size of the ferroelectric crystal, or reduce the domain wall density of the domain structure, thereby improving the transparency of the piezoelectric single crystal having high piezoelectric.

9 Claims, 4 Drawing Sheets

(51) Int. Cl.
H10N 30/06 (2023.01)
H10N 30/045 (2023.01)
H10N 30/87 (2023.01)

(56) References Cited

U.S. PATENT DOCUMENTS

| | | | | |
|---|---|---|---|---|
| 9,972,766 | B2* | 5/2018 | Yamashita | A61B 8/4444 |
| 2002/0036282 | A1* | 3/2002 | Chiang | C01G 23/006 |
| | | | | 117/949 |
| 2003/0021143 | A1* | 1/2003 | Nair | G11C 11/22 |
| | | | | 365/145 |
| 2003/0215865 | A1* | 11/2003 | Mayer | G01N 33/54373 |
| | | | | 435/6.19 |
| 2005/0072925 | A1* | 4/2005 | Chen | G01J 5/34 |
| | | | | 250/338.2 |
| 2005/0105038 | A1* | 5/2005 | Kondo | H10N 30/079 |
| | | | | 349/156 |
| 2006/0091353 | A1* | 5/2006 | Matsushita | H01L 41/18 |
| | | | | 117/948 |
| 2010/0327704 | A1* | 12/2010 | Sakamoto | H01L 41/273 |
| | | | | 29/25.35 |
| 2014/0062261 | A1* | 3/2014 | Yamamoto | H01L 41/25 |
| | | | | 29/25.35 |
| 2016/0248028 | A1* | 8/2016 | Huang | H01L 51/0002 |
| 2019/0071791 | A1* | 3/2019 | Luo | H01L 41/18 |
| 2020/0287123 | A1* | 9/2020 | Jiang | H01L 41/37 |

* cited by examiner

TRANSPARENT PIEZOELECTRIC SINGLE CRYSTAL PREPARATION METHOD

STATEMENT REGARDING FEDERALLY SPONSORED RESEARCH OR DEVELOPMENT

This invention was made with government support under Grant Nos. DMR1744213 and DMR1420620 awarded by the National Science Foundation. The Government has certain rights in the invention.

FIELD OF USE

The present invention relates to the technical field of piezoelectric materials, and in particular to a piezoelectric single crystal with near-perfect light transparency and high piezoelectricity, and a preparation method thereof, a photoacoustic transducer, a transparent actuator and an optical-electro-mechanical coupling device using the piezoelectric single crystal.

BACKGROUND OF THE INVENTION

Optoacoustic imaging is an emerging biomedical imaging technology. It combines the advantages of both rich optical contrast and high ultrasonic resolution. In the optoacoustic imaging, an object is illuminated with short laser pulses to generate an acoustic wave (namely optoacoustic signals) by means of thermoelastic effect. The signals are then detected by ultrasonic transducers and transformed into images using a series of algorithms. Thus, transparent piezoelectric transducers are required for simultaneously delivering light through the same path as the ultrasonic signals. Use of transparent piezoelectric transducers also opens up the possibility of ultrasonic particle manipulation with more complex optical systems (such as counter-propagating traps) and through-illumination imaging methods. Moreover, transparent piezoelectric materials can enable a wide range of transparent haptic sensors and actuators such as touch screens of cellular phones for self-charging of batteries from the touching, invisible robotic devices and so on.

However, achieving simultaneous high piezoelectricity and perfect transparency has long been a great challenge. The commonly-used transparent piezoelectric materials, $LiNbO_3$ crystals and polyvinylidene difluoride (PVDF) polymers, have excellent transparency, but low piezoelectric coefficients $d_{33}$ and electromechanical coupling factors $k_{33}$ ($d_{33}$-40 pC $N^{-1}$, $k_{33}$-47% for $LiNbO_3$, and $d_{33}$-20 pC $N^{-1}$, $k_{33}$-20% for PVDF), two of the most important material parameters for piezoelectric transducers and actuators. These drawbacks limit the performance of optoacoustic devices and significantly affect optoacoustic imaging quality, since optoacoustic signals collected within a crystal may be up to three orders of magnitude weaker than the signals detected in medical ultrasound imaging.

Perovskite solid solution ferroelectric ceramics and crystals with chemical compositions around their morphotropic phase boundaries (MPBs), such as $Pb(Zr,Ti)O_3$ (PZT) ceramics and domain-engineered $Pb(Mg_{1/3}Nb_{2/3})O_3$—$PbTiO_3$ (PMN-PT) crystals, possess extremely high $d_{33}$ and $k_{33}$ ($d_{33}$: 200-800 pC $N^{-1}$, $k_{33}$: 60-80% for perovskite solid solution ferroelectric ceramics and $d_{33}$: 1200-2500 pC $N^{-1}$, $k_{33}$: 90-95% for PMN-PT crystals), but they are usually opaque in the visible light spectrum due to the light scattering caused by high-density domain walls. There are two possible approaches to improve the transparency in perovskite solid solution ferroelectrics. The first is to pole a ferroelectric crystal along the polar direction to achieve a single domain state without domain walls. However, this will significantly degrade the piezoelectric performance. For example, the $d_{33}$ of [111]-poled rhombohedral PMN-PT crystals is only 100 pC $N^{-1}$, much lower than that of the rhombohedral PMN-PT crystals poled along the [001] non-polar direction ($d_{33}$: 1200-2500 pC $N^{-1}$). The second approach is to dramatically reduce their domain sizes by breaking the domains (hundreds of nanometers to tens of micrometers) into polar nano-regions (a few to tens of nanometers). Since the spatial sizes of these polar nano-regions are much smaller than the wavelength of the visible light spectrum, the light transparency of materials is efficiently improved, as observed in La-doped PZT. However, polar nano-regions without large domains will drastically reduce the remnant polarization, leading to a very low $d_{33}$ according to the equation $d_{33}=2Pr\varepsilon_{33}Q_{33}$ (Pr, the remnant polarization; $\varepsilon_{33}$, the dielectric permittivity; $Q_{33}$, the electrostrictive coefficient). These two approaches improve light transparency at the expense of piezoelectric performance. Therefore, optical functionalities in high-performance piezoelectric crystals and ceramics have not been realized and fully utilized despite more than 50 years of research efforts.

SUMMARY OF THE INVENTION

The objective of the present invention is to provide a piezoelectric single crystal and a preparation method and application thereof. The piezoelectric single crystal has both high piezoelectricity and good transparency simultaneously.

To achieve the above purpose, the present invention provides the following technical solutions.

A first aspect of the present invention provides a transparent piezoelectric single crystal with high piezoelectricity, where the piezoelectric single crystal is a binary/ternary relaxor-PT based ferroelectric crystal poled by an AC electric field.

Optionally, the structural formula of the binary/ternary relaxor-PT based ferroelectric crystal is $(Pb_{1-x}M_x)[(M_I, M_{II})_{1-y}Ti_y]O_3$ or $(Pb_{1-2x/3}M_x)[(M_I,M_{II})_{1-y}Ti_y]O_3$, where M is a rare earth cation including one or a combination of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er^{3+}$, $Tm^{3+}$, $Yb^{3+}$, and $Lu^{3+}$; $M_I$ includes one or a combination of $Mg^{2+}$, $Zn^{2+}$, $Ni^{3+}$, $Yb^{3+}$, $Sc^{3+}$, $In^{3+}$, $Co^{3+}$, and $Fe^{3+}$; $M_{II}$ includes one or a combination of $Nb^{5+}$ and $Ta^{5+}$; $0<x\leq0.05$; and $0.2<y<0.5$.

Optionally, the binary relaxor-PT based ferroelectric crystal includes lead titanate and a relaxor end member $Pb(M_I,M_{II})O_3$; and A-site Pb can be substituted by rare earth.

Optionally, the ternary relaxor-PT based ferroelectric crystal includes lead titanate and two relaxor end members of $Pb(M_I,M_{II})O_3$; and the ternary relaxor-PT based ferroelectric crystals include lead titanate, $PbZrO_3/PbHfO_3$ and a relaxor end member $Pb(M_I,M_{II})O_3$; and A-site Pb can be substituted by rare earth.

Optionally, the thickness of the piezoelectric single crystal is in the range of 0.05-5 mm.

A second aspect of the present invention provides a method for preparing a transparent piezoelectric single crystal with high piezoelectricity, including:

deposition of electrodes on two surfaces of binary/ternary relaxor-PT based ferroelectric crystal;

AC-poling the crystal through the electrodes using an AC electric field; and after polarization, removing the electrodes on both surfaces of the crystal, and then depositing Ag nanowires or ITO as electrodes on both surfaces of the crystal.

Optionally, before the deposition of electrodes on two surfaces of a piezoelectric material respectively, the method further includes:

Optionally, the frequency of the AC electric field is $0.1$-$10^2$ Hz, the amplitude is 0.5-3.0 kV mm$^{-1}$, and the number of cycles is 5-20.

Optionally, the interval between the cycles ranges from 0-60 seconds.

A third aspect of the present invention provides a photoacoustic transducer, including a component fabricated by the above-described AC-poled transparent piezoelectric single crystal with high piezoelectricity.

A fourth aspect of the present invention provides a transparent actuator, including a component fabricated by the above-described AC-poled transparent piezoelectric single crystal with high piezoelectricity.

A fifth aspect of the present invention provides an optical-electro-mechanical coupling device, including a component fabricated by the above-described AC-poled transparent piezoelectric single crystal with high piezoelectricity.

According to a specific embodiment provided by the present invention, the present invention discloses the following technical effects: the domain sizes of the binary/ternary relaxor-PT based ferroelectric crystals increase during poling using an AC electric field, greatly reducing the density of 71° domain walls that scatter light, thereby improving transparency of the binary/ternary relaxor-PT based ferroelectric crystals while maintaining high piezoelectricity.

BRIEF DESCRIPTION OF THE DRAWINGS

To describe the technical solutions in the embodiments of the present invention or in the prior art more clearly, the following briefly introduces the accompanying drawings required for describing the embodiments. Apparently, the accompanying drawings in the following description show merely some embodiments of the present invention, and a person of ordinary skill in the art may still derive other drawings from these accompanying drawings without creative efforts.

FIG. 1a is a domain structure diagram of an unpoled sample domain, FIG. 1b is a domain structure diagram of a DC-poled sample domain, and FIG. 1c is a domain structure diagram of an AC-poled sample domain;

DETAILED DESCRIPTION OF THE ILLUSTRATED EMBODIMENTS

The following clearly and completely describes the technical solutions in the embodiments of the present invention with reference to the accompanying drawings in the embodiments of the present invention. Apparently, the described embodiments are merely a part rather than all of the embodiments of the present invention. All other embodiments obtained by a person of ordinary skills in the art based on the embodiments of the present invention without creative efforts shall fall within the protection scope of the present invention.

The objective of the present invention is to provide piezoelectric single crystals that simultaneously possess near-perfect light transparency and high piezoelectricity, a method for their preparation, and concepts of devices that can be fabricated using these transparent piezoelectric crystals with high piezoelectricity.

To explain more clearly the foregoing objective, features, and advantages of the present invention, it is further described in details below with reference to the accompanying drawings and specific embodiments.

First, the present invention provides transparent piezoelectric single crystals with high piezoelectricity. They are binary/ternary relaxor-PT based ferroelectric crystals poled by an AC electric field. The general chemical formula of the binary/ternary relaxor-PT based ferroelectric crystals is $(Pb_{1-x}M_x)[(M_I,M_{II})_{1-y}Ti_y]O_3$ or $(Pb_{1-2x/3}M_x)[(M_I,M_{II})_{1-y}Ti_y]O_3$, where M is a rare earth cation including one or a combination of $La^{3+}$, $Ce^{3+}$, $Pr^{3+}$, $Nd^{3+}$, $Pm^{3+}$, $Sm^{3+}$, $Eu^{3+}$, $Gd^{3+}$, $Tb^{3+}$, $Dy^{3+}$, $Ho^{3+}$, $Er3+$, $Tm^{3+}$, $Yb^{3+}$, and $Lu^{3+}$; $M_I$ includes one or a combination of $Mg^{2+}$, $Zn^{2+}$, $Ni^{3+}$, $Yb^{3+}$, $Sc^{3+}$, $In^{3+}$, $Co^{3+}$, and $Fe^{3+}$; $M_{II}$ includes one or a combination of $Nb^{5+}$ and $Ta^{5+}$; $0<x\leq0.05$; and $0.2<y\leq0.5$. To more clarification, the binary relaxor-PT based ferroelectric crystal includes lead titanate and a relaxor end member $Pb(M_I,M_{II})O_3$. The ternary relaxor-PT based ferroelectric crystal includes lead titanate and two relaxor end members $Pb(M_I,M_{II})O_3$; or the ternary relaxor-PT based ferroelectric crystal includes lead titanate, $PbZrO_3/PbHfO_3$ (in this case, equivalent to $M_{II}=M_I$, which is $Zr^{4+}$ or $Hf^{4+}$), and a relaxor end member $Pb(M_I,M_{II})O_3$. Preferably, the thickness of the above piezoelectric single crystal is 0.05-5 mm.

Taking a rhombohedral perovskite relaxor ferroelectric crystal as an example, a polarized rhombohedral perovskite relaxor ferroelectric crystal, such as $Pb(Mg_{1/3}Nb_{2/3})O_3$—$PbTiO_3$ (PMN-PT), $Pb(Zn_{1/3}Nb_{2/3})O_3$—$PbTiO_3$ (PZN-PT)

exhibits an ultrahigh piezoelectric coefficient $d_{33}$ around the MPB composition. However, compared with conventional ferroelectric materials, the relaxor ferroelectric material has a relatively small domain size before polarization, which is on the order of about tens of nanometers according to previous transmission electronic microscopy (TEM) and piezoelectric force microscopy (PFM) experiments.

Figure 1:
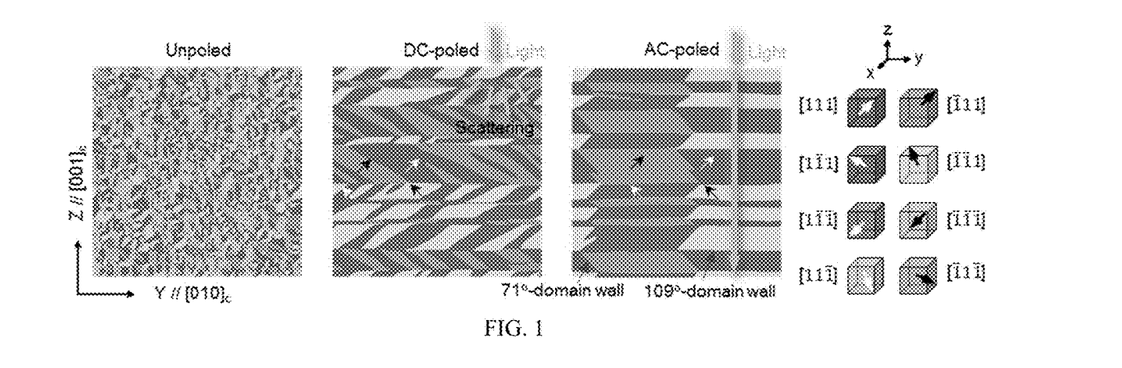
FIG. 1 is a domain diagram of rhombohedral PMN-28PT single crystals via DC and AC poling along the [001] direction according to an embodiment of the present invention using phase-field simulations, where

FIG. 1 is a phase field structure diagram of rhombohedral PMN-28PT single crystals via DC and AC poling along the [001] direction, where FIG. 1a is a domain structure of an unpoled sample, FIG. 1b is a domain structure of a DC-poled sample, and FIG. 1c is a domain structure of a AC-poled sample. Black and white vectors in the figure indicate the polarization direction, and black and white colors indicate a positive or negative polarization component along the [010] direction. These colors represent different ferroelectric domains, and the corresponding polarity directions are shown on the right side of the figure. Examples of the 71° and 109° domain walls are indicated by red arrows. Yellow arrows in FIGS. 1b and 1c are light beams, and FIG. 1c shows that light does not scatter when passing through an AC-poled sample.

Figure 2:
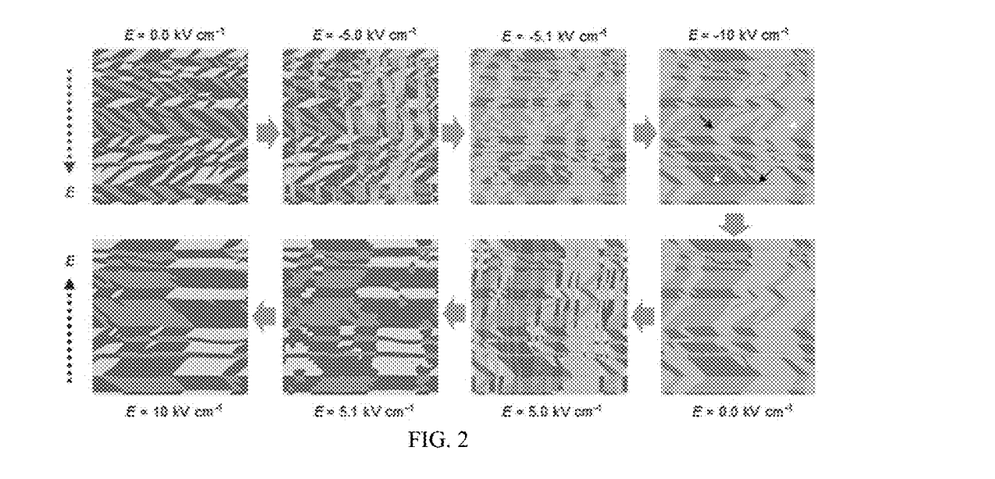
FIG. 2 is an evolution diagram of a domain pattern in a polarity inversion process under AC poling according to an embodiment of the present invention.
Figure 3:
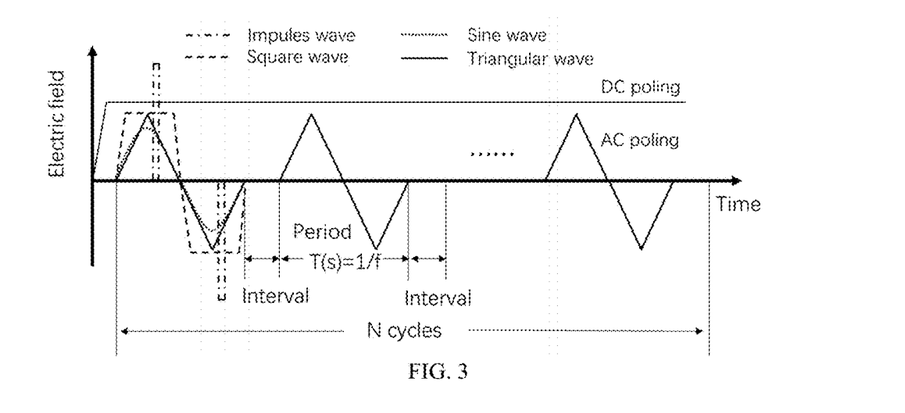
FIG. 3 is a waveform of an AC-DC electric field for AC and DC poling of a piezoelectric single crystal according to an embodiment of the present invention.

As shown in FIG. 1, in a conventional DC polarization method (DC electric field amplitude: 5 kV cm$^{-1}$; residence time: 5 minutes), a laminar structure with a larger average domain size is formed. However, as shown in FIG. 1b, the 71° domain walls within each laminar will lead to light scattering since the refractive indices $n_o$ and $n_e$ (the subscript letters "o" and "e" represent ordinary and extraordinary light, respectively) alternately as the light goes across a 71° domain wall. In the contrast, 109° domain walls do not induce light scattering since the refractive indices are the same for the domains on both sides of a 109° domain wall. In order to improve the transparency along the poling direction, 71° domain walls should be reduced as much as possible. As shown in FIG. 1c, repeatedly changing the polarity of the polarized electric field can increase the domain size of the ferroelectric crystal, or reduce the domain wall density of the domain structure. In this case, the 71° domain wall density is also significantly reduced. The present invention adopts the polarization of the AC electric field to control the domain structure, which increases the domain size and reduces the density of the 71° domain walls while maintaining the ultrahigh piezoelectricity, thereby further improving the transparency of the relaxor-based ferroelectric single crystal. An evolution process of the domain pattern of the AC-poled crystal is shown in FIG. 2. A waveform diagram of an AC electric field for AC poling is shown in FIG. 3.

Second, the present invention provides a method for preparing a transparent piezoelectric single crystal with high piezoelectricity. It includes:

depositing electrodes on two surfaces of a piezoelectric material, where the piezoelectric material is composed of a piezoelectric single crystal, and the piezoelectric single crystal is a binary/ternary relaxor-PT based ferroelectric crystal (which is the same as the binary/ternary relaxor-PT based ferroelectric crystal provided by the first aspect of the present invention);

AC-poling the crystal through the electrodes using an AC field; and removing the electrodes on both surfaces of the crystal after polarization, and then depositing Ag nanowires as electrodes on both surfaces of the crystal.

The specific preparation process is as follows:

The chemistry of the prepared piezoelectric single crystals belongs to a binary or ternary system composed of lead titanate (PbTiO$_3$; PT) and a relaxor end member such as Pb(M$_I$,M$_{II}$)O$_3$, where M$_I$ may be Mg$^{2+}$, Zn$^{2+}$, Ni$^{3+}$, Yb$^{3+}$, Sc$^{3+}$, In$^{3+}$, or the like, and M$_{II}$ may be Nb$^{5+}$, Ta$^{5+}$, etc., while lead (Pb) in the above binary/ternary system may be partially replaced by a rare earth element or the like. Methods for preparing such piezoelectric single crystals include a Bridgman method, a top seeded solution growth (TSSG) method, a horizontal Bridgman method, solid state conversion method and a Czochralski (CZ) method. The embodiment is not limited to the method for preparing the above-described piezoelectric single crystals. The piezoelectric single crystals were oriented by using X-ray diffraction with x, y and z axis along [100], [010] and [001] directions respectively, and then cut into various dimensions by using a diamond blade or wire saw. The thickness of the piezoelectric single crystal was in the range of 0.05-5 mm. Vacuum-sputtered gold or baked silver was applied to both faces of the samples as electrodes.

The appropriate frequency, the peak amplitude of electric field, and the number of cycles were chosen according to the size and composition of the crystals. In the embodiment, the above piezoelectric single crystals were poled by an AC electric field with a frequency of 0.1-10$^2$ Hz, a peak amplitude of 0.5-3.0 kV mm$^{-1}$, and the number of cycles of 5-20. The waveforms of an AC electric field include sine wave, triangular wave, square wave, impulse wave and other waves with the polarity of electric field alternating between negative and positive continuously. The intervals (the time between two cycles) were ranging from 0-60 seconds.

The piezoelectric coefficients were determined by a combination of a quasi-static $d_{33}$-meter (ZJ-6A) and the electric-field-induced strain. The electric-field-induced strain was measured by a ferroelectric test system (TF Analyzer 2000E, aixACCT, German) with a laser interferometer (SIOS SP-S 120E, German). The dielectric permittivities were measured using an LCR meter (E4980A, KEYSIGHT technologies, CA, USA). After electric measurements, the electrodes were removed by chemical or physical methods without affecting the polarization. The crystal surfaces were then carefully polished to optical quality using diamond polishing paste with decreasing average grit size down to 0.05 μm. Transmission spectra were then measured by a UV-VIS-IR spectrophotometer (JASCO V-570, Japan) at the wavelength ranging from 300 to 2500 nm. The incident light was set to transmit through the crystal along the poling direction, which was perpendicular to the crystal surface. The domain patterns and their extinction behavior were observed by using a polarizing light microscope (PLM) pair (OLYMPUS BX51, Japan) with 0°/90° crossed polarizers/analyzers (P/A). The optical retardation was measured by using a thick-Berek compensator (OLYMPUS U-CTB ranging from 0-10λ) and an interference filter (IF546, λ=546.1 nm). The birefringence was calculated by dividing the retardation by the samples' thicknesses.

EXAMPLE 1

Transparent PMN-28PT Single Crystals Poled By an AC Electric Field

Figure 4:
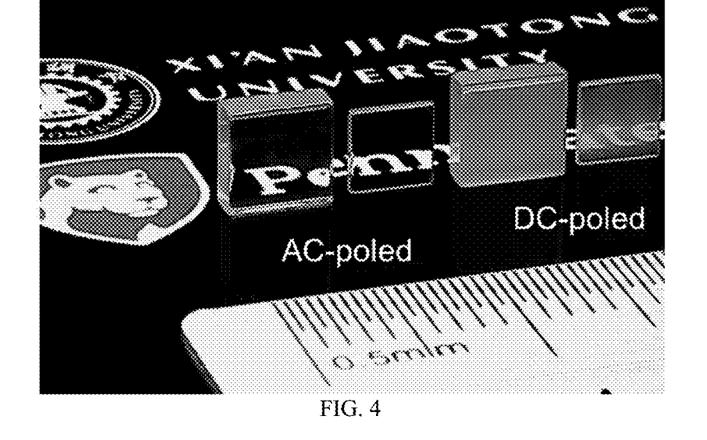
FIG. 4 is a physical diagram of a PMN-28PT crystal poled by an AC electric field and a PMN-28PT crystal poled by a DC electric field according to an embodiment of the present invention.
Figure 5:
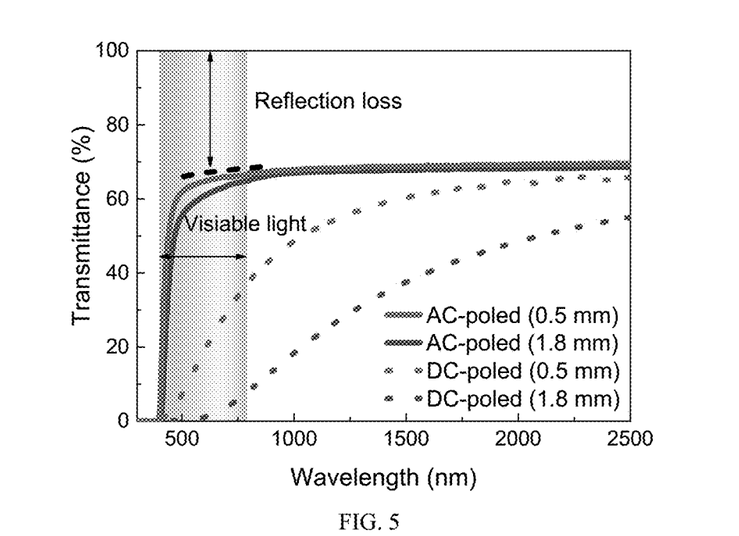
FIG. 5 is a curve diagram of light transmittance of a PMN-28PT crystal after AC poling and DC poling according to an embodiment of the present invention.
Figure 6:
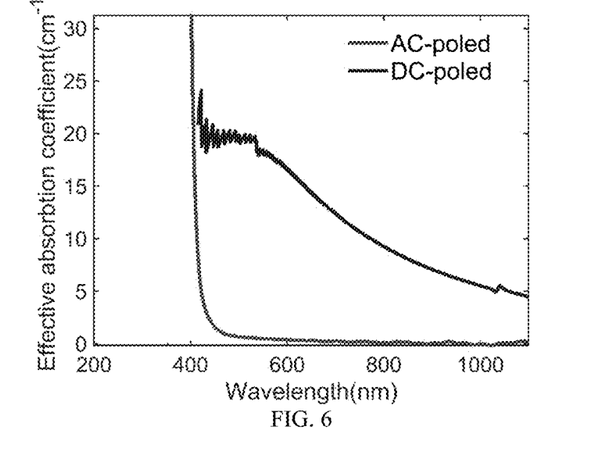
FIG. 6 is a curve diagram of effective light absorption coefficients of AC-poled and DC-poled PMN-28PT crystals according to an embodiment of the present invention.

FIG. 4 shows transparent PMN-28PT piezoelectric single crystals of different thicknesses, where the crystals have thicknesses of 0.5 mm and 1.8 mm, respectively. As can be seen from FIG. 4, the crystals have good transparency after being poled by an AC electric field. The light transmittance of the AC-poled samples is found to be very close to its theoretical limit (light is only reflected by the two surfaces of the sample), as shown in FIG. 5. It should be noted that the light with wavelength below 400 nm is completely absorbed due to the optical absorption edge (−3.10 eV), which is similar to most oxygen-octahedral perovskites. At the wavelength above 400 nm, the light absorption coefficient of AC-poled samples is found to be almost zero while the light absorption coefficient of DC-poled samples is quite large and exhibits a monotonic decrease with increasing wavelength, as shown in FIG. 6.

Figure 7:
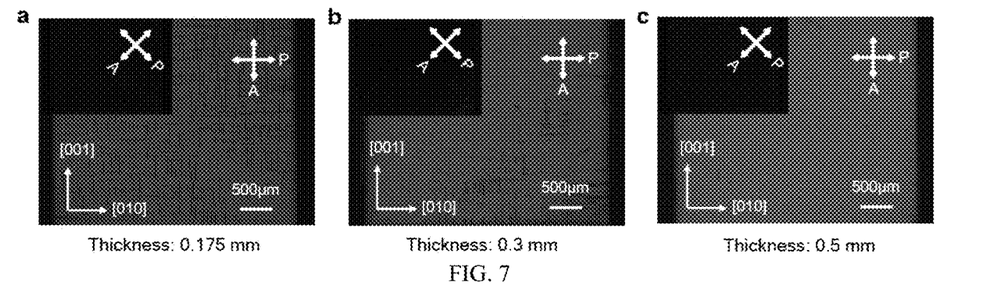
FIG. 7 is a polarizing light microscope (PLM) diagram of AC-poled PMN-28PT crystals of different thicknesses according to an embodiment of the present invention.

PLM images of transparent PMN-PT single crystals with different thicknesses were also given in FIG. 7. By increasing the thickness of the sample, cross-like domain walls can be totally eliminated. This phenomenon is thought to be associated with the clamping effect and damage layers around the surfaces of the samples. These two factors are prominent for the thin samples, which may prohibit the growth of a ferroelectric domain. The AC-poling method is more effective to obtain transparent PMN-PT single crystals when the thickness is beyond 0.2 mm.

EXAMPLE 2

Transparent PMN-30PT Single Crystals Poled By an AC Electric Field

Figure 8:
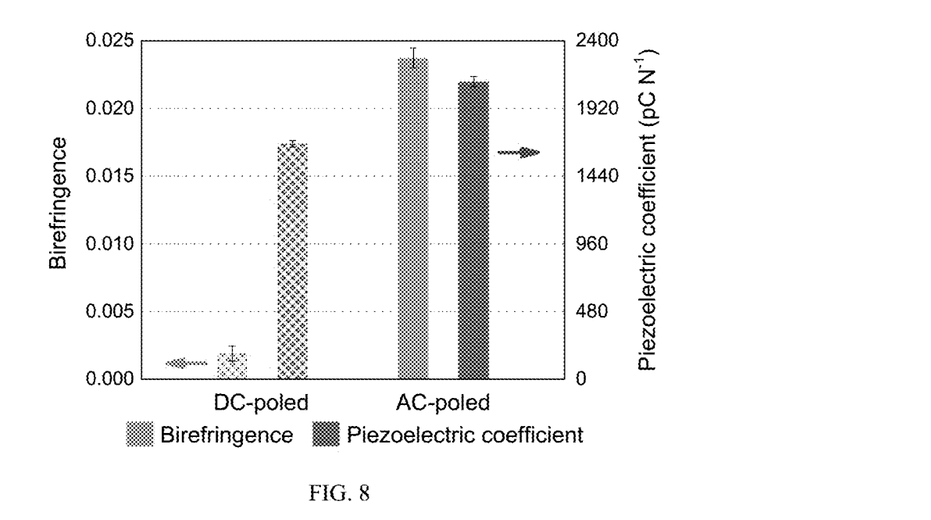
FIG. 8 is a curve diagram showing a piezoelectric coefficient $d_{33}$ and a birefringence of AC-poled and DC-poled PMN-28PT crystals according to an embodiment of the present invention.

Table I lists the principle properties of transparent PMN-30PT single crystals poled by an AC electric field, including free and clamped dielectric permittivity, dielectric loss, piezoelectric coefficients, electromechanical coupling factors, Curie and phase transition temperatures and electro-optic coefficients. It can be observed that transparent PMN-30PT single crystals maintain excellent piezoelectric performance, even superior to the crystals poled by a DC electric field, as shown in FIG. 8, where the thickness of the crystal in FIG. 8a is 0.175 mm; the thickness of the crystal in FIG. 8b is 0.3 mm; and the thickness of the crystal in FIG. 8c is 0.5 mm.

TABLE I

Properties of AC- and DC-poled PMN-30PT single crystals

| Properties of PMN-30PT | DC-poled | AC-poled |
|---|---|---|
| Free dielectric permittivity | 5800 | 7400 |
| Clamped dielectric permittivity | 830 | 910 |
| Dielectric loss | 0.0048 | 0.003 |
| Piezoelectric coefficient (pC/N) | 1670 | 2100 |
| Electromechanical coupling coefficient $k_{33}$ | 0.925 | 0.936 |
| Phase transition temperature $T_{RT}$ (° C.) | 97 | 96 |
| Curie temperature $T_C$ (° C.) | 138 | 138 |
| Transmittance (%) @633 nm | 34.6 | 66.7 |
| Longitudinal effective electro-optic coefficient $\gamma^L_c$* (pm/V) @633 nm light beam//[001] | — | 153 |
| Electro-optic coefficient $\gamma_{33}$* (pm/V) @633 nm light beam//[110] | — | 227 |
| Electro-optic coefficient $\gamma_{13}$* (pm/V) @633 nm light beam//[110] | — | 115 |
| Transverse effective electro-optic coefficient $\gamma^T_c$* (pm/V) @633 nm light beam//[110] | — | 93 (Cal.) |

EXAMPLE 3

Birefractive Indexes of AC- and DC-Poled PMN-30PT Single Crystals

The birefractive index of AC-poled crystals is about one order of magnitude higher than that of DC-poled counterparts, as shown in FIG. 8 and Table 2. This difference is associated with different domain structures in AC-poled and DC-poled crystals. The principle axis of optical indicatrices of the domains on both sides of a 71° domain wall are perpendicular to each other on the (001) plane, which will result in the cancellation of birefractive index. For AC-poled crystals, the birefractive index is approximately equal to the intrinsic value of a single domain rhombohedral PMN-28PT due to the substantially decreased number of 71° domain walls. On the contrary, DC-poled crystals have the much lower birefractive index due to the cancellation effect of the birefractive index.

TABLE II

Birefractive index measurements of AC- and DC-poled PMN-30PT single crystals

| PMN-30PT | Thickness (mm) | Theta1 (°) | Theta2 (°) | Theta (°) | Retardation | Birefringence |
|---|---|---|---|---|---|---|
| AC-poled | 0.175 | 46.40 | 15.60 | 15.40 | 4038.39 | 0.0231 |
| | 0.175 | 45.40 | 13.70 | 15.85 | 4275.37 | 0.0244 |
| | 0.175 | 46.55 | 14.70 | 15.93 | 4315.51 | 0.0247 |
| | 0.175 | 44.70 | 14.00 | 15.35 | 4012.46 | 0.0229 |
| | 0.175 | 45.55 | 14.64 | 15.46 | 4064.40 | 0.0232 |
| | 0.175 | 45.70 | 13.85 | 15.93 | 4315.51 | 0.0247 |
| | 0.175 | 45.40 | 14.49 | 15.46 | 4064.40 | 0.0232 |
| DC-poled | 0.175 | 36.10 | 25.05 | 5.53 | 473.34 | 0.0027 |
| | 0.175 | 30.30 | 21.60 | 4.35 | 325.04 | 0.0019 |
| | 0.175 | 37.00 | 26.75 | 5.13 | 451.10 | 0.0026 |
| | 0.175 | 34.40 | 25.20 | 4.60 | 363.48 | 0.0021 |
| | 0.175 | 33.78 | 25.95 | 3.92 | 261.33 | 0.0015 |
| | 0.175 | 33.75 | 26.60 | 3.58 | 219.62 | 0.0013 |
| | 0.175 | 33.90 | 26.65 | 3.63 | 225.81 | 0.0013 |

EXAMPLE 4

Figure 9:
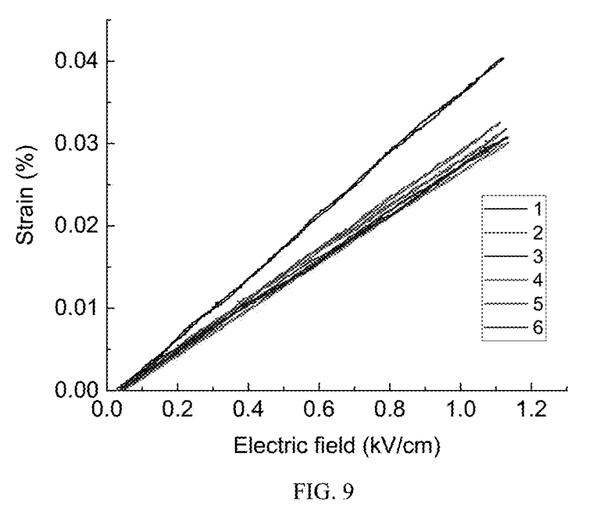
FIG. 9 is a diagram showing electric field induced strains of a transparent PIN-PMN-PT single crystal having an MPB composition according to an embodiment of the present invention.
Figure 10:
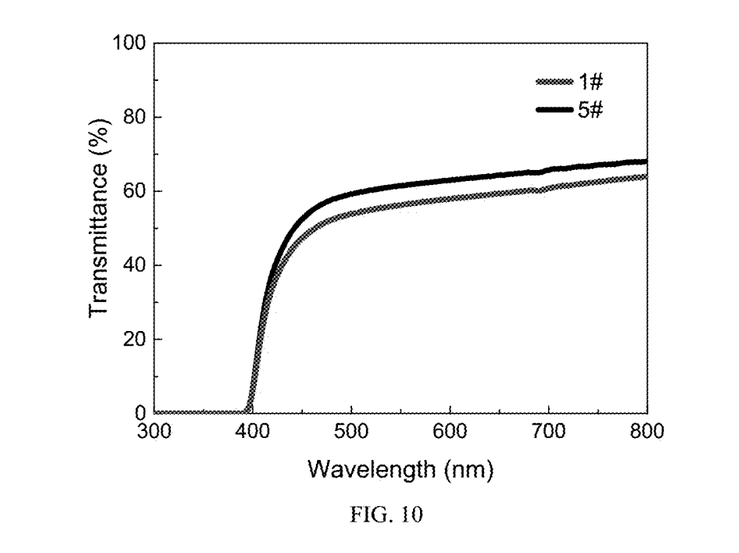
FIG. 10 is a diagram showing the light transmittance of a transparent PIN-PMN-PT single crystal having an MPB composition according to an embodiment of the present invention.

Ultrahigh-Piezoelectric-Performance Transparent $Pb(In_{1/2}Nb_{1/2})$-$Pb(Mg_{1/3}Nb_{2/3})O_3$—$PbTiO_3$ (PIN-PMN-PT) Single Crystals With Composition Around MPB Table III lists the dielectric and piezoelectric properties for transparent PIN-PMN-PT single crystals with compositions around the MPB. The phase transition temperatures are in a range of 100-105° C., and the Curie temperatures are in a range of 170-175° C. The piezoelectric coefficients are higher than 2800pC/N after AC-poling. The Electric field induced strains and the light transmittance are given in FIG. 9 and FIG. 10.

TABLE III

Dielectric and piezoelectric properties of transparent PIN-PMN-PT single crystals with compositions around MPB

| PIN-PMN-PT | Free dielectric permittivity | Dielectric loss | Clamped dielectric permittivity | Piezoelectric coefficient (pC/N) |
|---|---|---|---|---|
| #1 | 9252 | 0.0100 | 803 | 3547 |
| #2 | 8934 | 0.0067 | 776 | 3317 |
| #3 | 8735 | 0.0040 | 748 | 2955 |
| #4 | 8696 | 0.0074 | 885 | 2903 |
| #5 | 8552 | 0.0035 | 784 | 2880 |
| #6 | 8873 | 0.0038 | 798 | 3093 |

Third, the present invention provides ideas for the photoacoustic transducers that include components fabricated by the transparent piezoelectric single crystals with high piezoelectricity.

Fourth, the present invention provides ideas for transparent actuators that include components fabricated by the transparent piezoelectric single crystals with high piezoelectricity.

Fifth, the present invention provides ideas for optical-electro-mechanical coupling devices that include components fabricated by the transparent piezoelectric single crystals with high piezoelectricity.

Each embodiment of the present specification is described in a progressive manner, each embodiment focuses on the difference from other embodiments, and the same and similar parts between the embodiments may refer to each other.

Several examples are provided for illustrating the principles and implementation methods of the present invention. The descriptions of the embodiments are used to help illustrate the method and its core principles of the present invention. In addition, those skilled in the art can make various modifications in terms of specific embodiments and scope of application in accordance with the discoveries of the present invention. In conclusion, the content of this specification shall not be construed as a limitation to the present invention.

What is claimed is:

1. A method of preparing a piezoelectric single crystal which exhibits piezoelectricity and transparency, comprising the steps of:
    depositing electrodes on two opposition surfaces of a piezoelectric material respectively, wherein the piezoelectric material is a piezoelectric single crystal, and the piezoelectric single crystal is a ferroelectric crystal;
    reducing density of 71° domain walls of the piezoelectric single crystal by using an AC electric field to polarize the piezoelectric single crystal through the electrodes, to make the piezoelectric single crystal exhibit transparency while maintaining piezoelectricity; and
    after polarization is completed, removing the electrodes on the two opposition surfaces of the piezoelectric single crystal and then depositing Ag nanowire or indium tin oxide (ITO) as electrodes on the two opposition surfaces of the piezoelectric single crystal.

2. The method according to claim 1, wherein, before depositing the first two electrodes on the two opposition surfaces of the piezoelectric single crystal, the method further comprises
    forming the piezoelectric material to a desired thickness.

3. The method according to claim 2, wherein the piezoelectric material is formed having a thickness in a range from 0.05-5 mm.

4. The method according to claim 1, wherein a frequency range of the applied AC electric field is $0.1$-$10^2$ Hz, an amplitude range of the applied AC electric field is 0.5-3.0 kV $mm^{-1}$, and a number of cycles performed ranges from 5-20.

5. The method according to claim 2, wherein a frequency range of the applied AC electric field is $0.1$-$10^2$ Hz, an amplitude range of the applied AC electric field is 0.5-3.0 kV $mm^{-1}$, and a number of cycles performed ranges from 5-20.

6. The method according to claim 3, wherein a frequency range of the applied AC electric field is $0.1$-$10^2$ Hz, an amplitude range of the applied AC electric field is 0.5-3.0 kV $mm^{-1}$, and a number of cycles performed ranges from 5-20.

7. The method according to claim 4, wherein an interval between the cycles ranges from 0-60 seconds.

8. The method according to claim 5, wherein an interval between the cycles ranges from 0-60 seconds.

9. The method according to claim 6, wherein an interval between the cycles ranges from 0-60 seconds.

* * * * *

UNITED STATES PATENT AND TRADEMARK OFFICE
CERTIFICATE OF CORRECTION

PATENT NO. : 11,758,818 B2
APPLICATION NO. : 16/541309
DATED : September 12, 2023
INVENTOR(S) : Fei Li et al.

It is certified that error appears in the above-identified patent and that said Letters Patent is hereby corrected as shown below:

On the Title Page

Item (73)
Second assignee listed as The Pennsylvania State University; should be listed as PENN STATE RESEARCH FOUNDATION.

Signed and Sealed this
Twentieth Day of August, 2024

Katherine Kelly Vidal
*Director of the United States Patent and Trademark Office*